United States Patent
Rashid

Patent Number: 5,460,525
Date of Patent: Oct. 24, 1995

[54] DUAL MATRIX BAND RETAINER

[76] Inventor: Paul L. Rashid, 3318 W. Howell Rd., Mason, Mich. 48854

[21] Appl. No.: 206,827

[22] Filed: Mar. 7, 1994

[51] Int. Cl.$^6$ .................................................. A61C 5/04
[52] U.S. Cl. ............................................ 433/155; 433/39
[58] Field of Search ............................ 433/39, 153, 154, 433/155, 156

[56] References Cited

U.S. PATENT DOCUMENTS

| | | | |
|---|---|---|---|
| 701,799 | 6/1902 | Crenshaw | 433/39 |
| 1,990,381 | 2/1935 | Ivory. | |
| 2,439,703 | 4/1948 | Tofflemire. | |
| 2,466,830 | 4/1949 | Tofflemire. | |
| 2,502,903 | 4/1950 | Tofflemire. | |
| 2,663,935 | 12/1953 | Walser | 433/39 |
| 2,686,970 | 8/1954 | Reiter. | |
| 2,805,477 | 9/1957 | Howard | 433/39 |
| 3,237,307 | 3/1966 | Tofflemire. | |
| 3,305,928 | 2/1967 | Tofflemire. | |
| 3,462,841 | 8/1969 | Ainsworth. | |
| 3,516,162 | 6/1970 | Ainsworth. | |
| 3,613,245 | 8/1971 | Knight. | |
| 4,202,103 | 5/1980 | Zall et al. | 433/154 |
| 4,915,627 | 4/1990 | Hirdes | 433/155 |
| 5,055,045 | 8/1991 | Dickie et al. | 433/155 |
| 5,114,341 | 5/1992 | Kassel | 433/39 |

FOREIGN PATENT DOCUMENTS

| | | | |
|---|---|---|---|
| 1002539 | 10/1951 | France | 433/39 |
| 1056323 | 4/1959 | Germany | 433/39 |

Primary Examiner—Cary E. O'Connor

[57] ABSTRACT

A dual dental matrix band retainer for use in dentistry comprising a first matrix band retainer which is connected to a second matrix band retainer. Each matrix band retainer is provided with a matrix band which is looped around a different posterior tooth in the same quadrant of a patient's mouth. Each matrix band retainer can be operated independently and separably of each other which allows for the dentist to restore two posterior teeth simultaneously. As a result, the time required for the dentist to restore both posterior teeth is greatly diminished improving the work productivity of the dentist while maximizing the comfort to the patient.

2 Claims, 3 Drawing Sheets

DUAL MATRIX BAND RETAINER

TECHNICAL FIELD

This invention relates generally to instruments used by the dental profession and in particular to dental matrix band retainers which are used to temporarily retain matrix bands tightly around a tooth following cavity preparation so that amalgams, composite resins, or temporary dressings may be inserted.

BACKGROUND OF THE INVENTION

When working on molars and bicuspids following cavity preparation, a dentist usually uses a dental matrix band which is held tightly around a tooth using a dental matrix band retainer so that the filling will restore the natural contour of the tooth. The matrix band, as described in U.S. Pat. No. 2,466,830 to Tofflemire, is a metal strip which is usually folded diagonally intermediate of its length to produce two ends that are arranged in diverging relation with one another when the strip is flat. The matrix band is slipped around the single tooth with the free ends extending in parallel and approximate relation with one another from the central portion of the buccal aspect and the fold arranged on the lingual side of the molar or bicuspid. The matrix band is pressed down until it is disposed close to the gingival border. Once slipped around the tooth, the matrix band is tightened around the tooth by using a matrix band retainer.

Over the years, many matrix band retainers has been developed. Most recently, U.S. Pat. No. 5,055,045 to Dickie et al. discloses a disposable plastic matrix band retainer which can be unlocked from its tightened position over a single tooth within a mouth quadrant without releasing the matrix band from the retainer. Once removed, the entire plastic matrix band retainer must be discarded.

U.S. Pat. No. 4,915,627 to Hirdes discloses a matrix band retainer comprising a frame, a threaded rod screwingly displaced in the frame, a coulisse block arranged which holds a matrix band and a tightening spring which is held on the threaded rod and acts upon a quick tightening nut. Once place around a single tooth, the matrix band is tightened by tilting a quick tightening nut which slides the coulisse block in the longitudinal direction. Once this coarse adjustment is made, a fine adjustment is available by rotating a knob located at one end of the threaded rod.

U.S. Pat. No. 3,613,245 to Knight discloses a similar matrix band retainer in which the looped matrix band is passed through a recess in a movable block. Simplicity of design allows the movable block to be easily removed and replaced. Rotation of a sleeve moves the block and decreases the size of the looped matrix band around a single tooth.

U.S. Pat. Nos. 3,462,841 and 3,516,162 to Ainsworth describe a similar matrix band retainer in which the matrix band is provided with enlargements on the ends such which are pulled in order to tighten the matrix band around a single tooth. The matrix band retainer incorporates a tubular body which protects the lips against moving parts within the body.

U.S. Pat. Nos. 2,439,703 and 2,502,903 describe the Tofflemire Matrix Retainer which consists of a slidably mounted clamping block with a diagonally extending slot into which the ends of the looped matrix band are inserted. The ends of the matrix band are clamped against the block by rotating a knob. Once the matrix band is clamped in the block, the matrix band is looped around a single tooth. A wedge may be inserted between the tooth being treated and an adjacent tooth to allow inserting the matrix band around the tooth easier. The tightness of the matrix band around the single tooth can be adjusted by rotating a sleeve which retracts the block.

Although many matrix band retainers have been developed, they all have the same limitation in that only a single tooth may be treated at one time. In other words, if a dentist needs to restore two posterior teeth with Class II, III or IV carious lesions in the same quadrant of a patient's mouth, the dentist must treat each tooth separately by performing the same procedure on each tooth in a sequential manner. As a result, the amount of time required to restore both teeth is approximately twice the amount of time needed to treat a single tooth which diminishes the work productivity of the dentist and the comfort to the patient.

SUMMARY OF THE INVENTION

It is an object of the present invention to provide a dual matrix band retainer which allows for the restoration of two posterior teeth with Class II, III or IV carious lesions simultaneously in the same quadrant of a patient's mouth.

It is another object of the invention to reduce the amount required for a dentist to treat two teeth in the same quadrant of a patient's mouth and thereby improving the work productivity of the dentist and maximizing the comfort to the patient.

In keeping with these objects and with others which will become apparent hereinafter, an embodiment of the invention resides, briefly stated, in a dual matrix band retainer which is formed by a fastening means connecting the first and second matrix band retainers. Preferably, the fastening means provides sufficient rigidity so that the first and second matrix band retainers can cooperate integrally as a dual matrix band retainer. The first and second matrix band retainers are aligned along a longitudinal axis so that the dual matrix band retainer can comfortably fit inside the oral cavity of a patient's mouth.

With the present invention, a dentist can restore two posterior teeth with Class II, III or IV carious lesions in the same quadrant simultaneously by looping the matrix bands from each matrix band retainer around each tooth to be restored. Once looped around each tooth, the matrix bands are then tightened by turning a knob near the end of each matrix band retainer. Once each tooth has been restored, the dentist removes each matrix band retainer by loosening the matrix bands around each tooth.

According to the embodiment of the present invention, the time necessary for restoring two posterior teeth with Class II, III or IV carious lesions in the same quadrant of a patient's mouth is greatly reduced. The reason is that it is no longer necessary for the dentist to completely restore one Class II, III or IV carious lesion before being able to restore another Class II, III or IV carious lesion. As a result, the work productivity of the dentist is increased, as well as, the comfort to the patient.

Other objects, features and advantages of the invention will become apparent from the following detailed description taken in conjunction with the drawings and appended claims.

BRIEF DESCRIPTION OF THE DRAWINGS

The invention will now be described with reference to the drawings wherein.

DETAILED DESCRIPTION OF THE INVENTION

Figure 1:
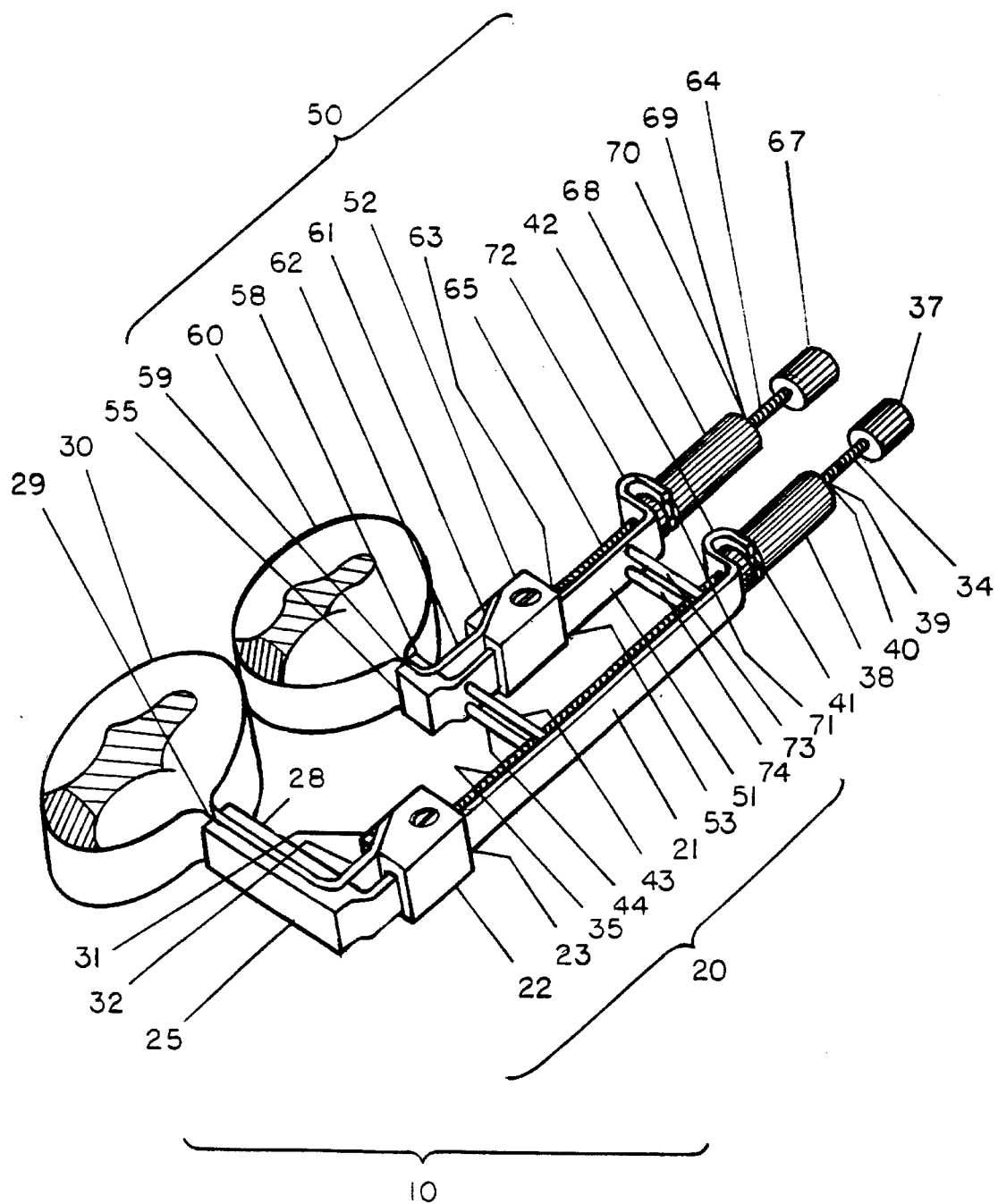
FIG. 1 is an isometric view of the dual matrix band retainer in use in accordance with an embodiment of the present invention.
Figure 2:
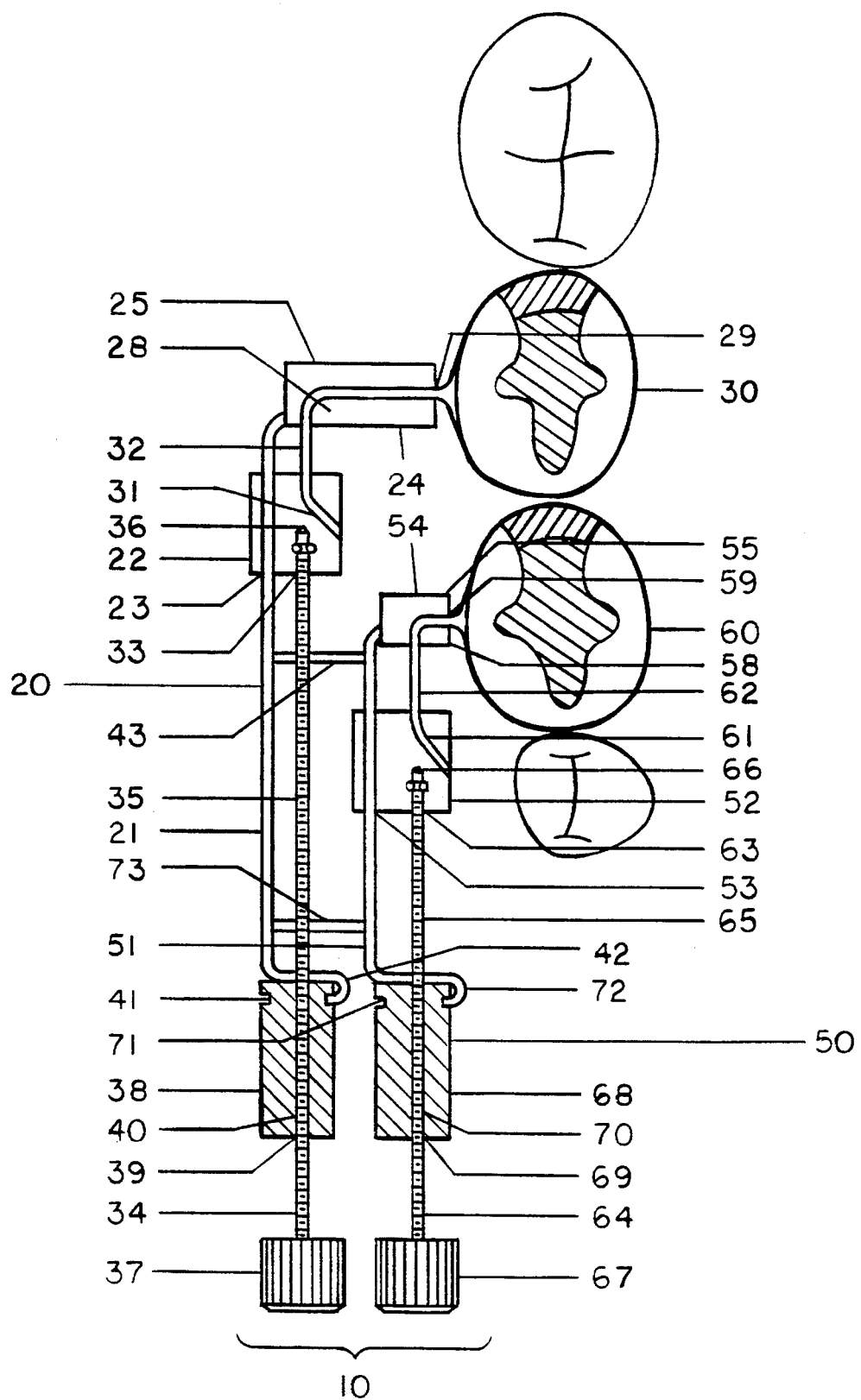
FIG. 2 is a top plan view of a dual matrix band retainer in use, parts being shown in section, in accordance with an embodiment of the present invention.

A dual matrix band retainer 10 is illustrated in FIGS. 1 and 2. In general, the dual matrix band retainer 10 includes a first matrix band retainer 20 connected to a second matrix band retainer 50. In the preferred embodiment, each matrix band retainer 20 and 50, for example, are similar to the type as described in U.S. Pat. No. 2,502,903, which is herein incorporated by reference. However, it should be understood that other types of matrix band retainers, which are well known in the art, may be used without changing the scope and spirit of the present invention.

In a typical arrangement as shown in FIG. 1, the dual matrix band retainer 10 is in position for restoring, for example, two disto-occlusal cavity preparations situated between the lower right second bicuspid and third molar. Each matrix band retainer 20 and 50 includes a longitudinally extending bar 21 and 51 on which a matrix band clamping blocks 22 and 52 may be slidably mounted. As shown in FIG. 1, each block 22 and 52 are fashioned with a guideway 23 and 53 adapted to receive the bars 21 and 51, respectively. It should be noted that, in the present invention, bar 21 is much longer in the axial direction than bar 51 to enable the first matrix band retainer 20 to treat a different tooth than the second matrix band retainer 50. Each matrix band clamping block 22 and 52 has a diagonally-extending slot 31 and 61, respectively, in order to receive the end sections 32 and 62 of each matrix band 30 and 60.

Each bar 21 and 51 includes a head portion 24 and 54, respectively. Head portion 24 defines two fingers 25 and 28. Likewise, head portion 54 defines two fingers 55 and 58. As best seen in FIG. 2, fingers 25 and 28 of head portion 24 are longer than corresponding fingers 55 and 58 of head portion 54 so that the ends 29 and 59 of head portions 24 and 54 are aligned along the same longitudinal axis. Aligning the head portions 24 and 54 in the same longitudinal axis permits the dual matrix band retainer 10 to occupy a minimum amount of space and, in turn, allows the dual matrix band retainer be inserted in a patient's mouth comfortably. It should be noted that, in the present invention, the angle of head portions 24 and 54 is a design choice, since head portions 24 and 54 may be at any identical angle and still lie along the same longitudinal axis.

Each matrix band retainer 20 and 50 is designed to hold a matrix band that can encircle any two adjacent posterior teeth or two posterior teeth separated by another posterior tooth in the same quadrant of a patient's mouth. As shown in FIGS. 1 and 2, matrix band 60 encircles the lower right first molar and matrix band 30 encircles the lower right second molar. It should be understood that the relative length of each matrix band is not important and only needs to be of sufficient length to permit each band to be looped around the appropriate posterior tooth (bicuspid or molar) and allow the end sections 32 and 62 of each matrix band to be received in the slots defined between the fingers 25, 28 and 55, 58 and secured in each matrix band clamping block 22 and 52. When the ends of each matrix band 32 and 62 are received in the fingers of each matrix band retainer, the loops of each matrix band will extend laterally from each matrix band retainer 20 and 50.

As best seen in FIG. 2, each matrix band clamping block 22 and 52 has a longitudinally-extending threaded bore 33 and 63 which intersects the slots 31 and 61, respectively. Spindles 34 and 64 have a threaded portion 35 and 65 that is received in each bore 33 and 63, respectively, and each spindle has a conical end 36 and 66. Each spindle may be rotated in each bore, separately and independently of each other, by operating knobs 37 and 67 to cause each conical head to clamp the ends 32 and 62 of each matrix band in the matrix band clamping blocks 22 and 52. It should be noted that a movement of each matrix clamping block along each bar 21 and 51 will move the matrix ends 32 and 62 therewith. As best seen in FIG. 1, when each matrix band clamping block is moved to the right, each matrix band will tighten around each tooth, while movement to the left will loosen each matrix band around each posterior tooth.

The means for moving each matrix band clamping block 22 and 52 axially after it has clamped the matrix band ends 32 and 62 to each matrix band clamping block comprises tightening screws 38 and 68, respectively. Each tightening screw has a bore 39 and 69 with a threaded portion 40 and 70, respectively, for receiving each threaded spindle. Each tightening screw has an annular groove 41 and 71 therein for receiving the forks of U-shaped ends 42 and 72, respectively. Each tightening screw 38 and 68 may be rotated in one direction, separately and independently of each other, to advance each matrix clamping block 22 and 52 towards each head 24 and 54, respectively, while a rotation of each tightening screw in the opposite direction will retract each matrix band clamping block. It should be understood that each end 42 and 72 holds each tightening screw against longitudinal movement, but permits its free rotation.

As best shown in FIG. 1, the dual matrix band retainer 10 is formed by connecting a first matrix band retainer 20 to a second matrix band retainer 50. Preferably, bars 21 and 51 are connected by rods 43, 44, 73 and 74 so that the first matrix band retainer 20 and the second matrix band retainer 50 are rigidly affixed. Rods 43 and 44 are aligned on the same vertical plane, as well as, rods 73 and 74. The location of rods 43, 44, 73 and 74 on each bar 21 and 51 permit each matrix band clamping block to slide freely without interference from the rods. Connecting matrix band retainers 20 and 50 in this manner permits the integral cooperation necessary for the dual matrix band retainer 10 to act as a single device to treat two posterior teeth simultaneously in the same quadrant of a patient's mouth.

It should be noted that, in the present invention, the fastening means for connecting each matrix band retainer 20 and 50 may be connected at various other locations on each matrix band retainer by using any typical fastening means known in the industry to allow each matrix band retainer to rigidly cooperate as a dual matrix band retainer.

Figure 3:
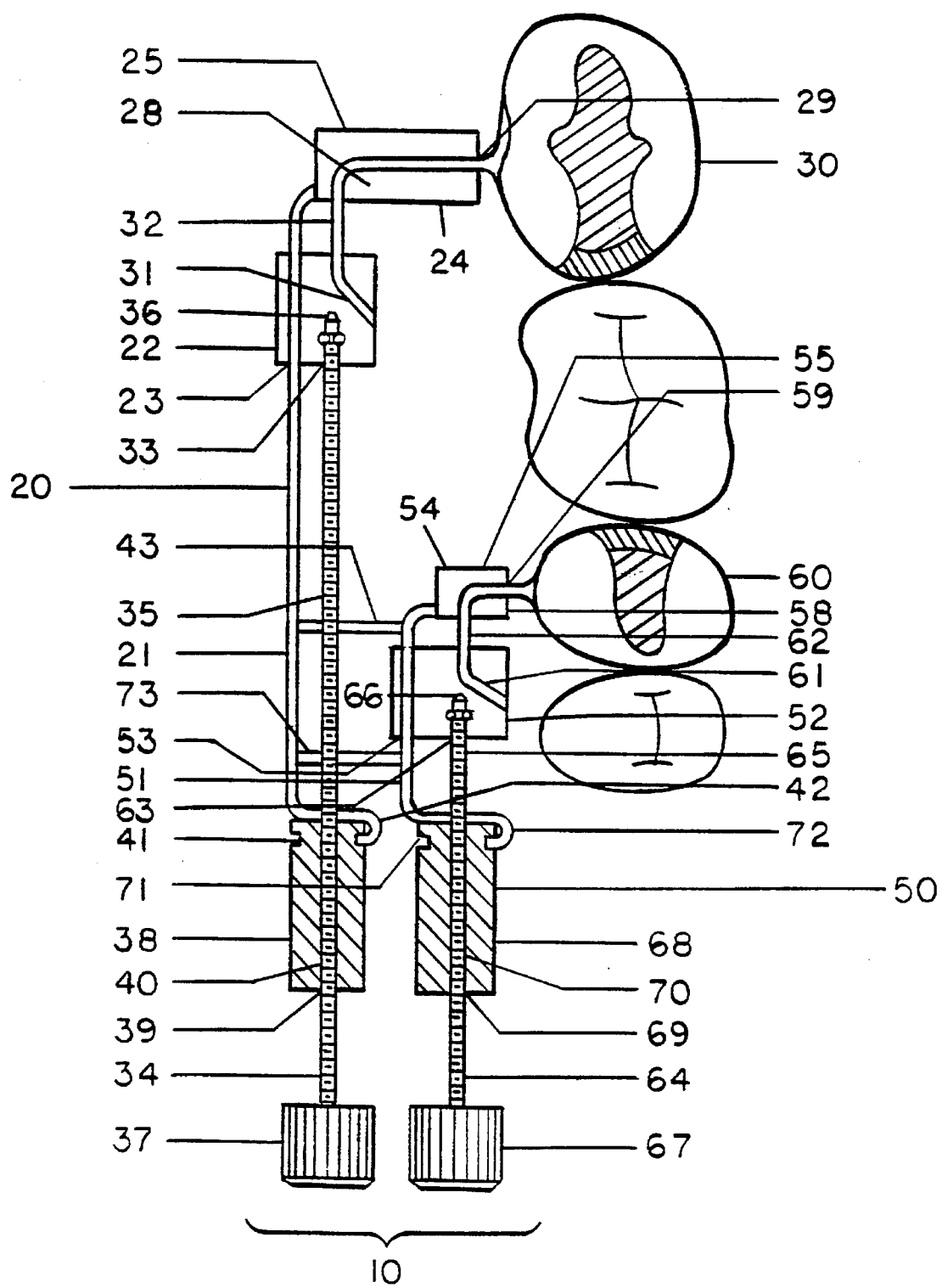
FIG. 3 is another top plan view of a dual matrix band retainer in use, parts being shown in section, in accordance with an embodiment of the present invention.

In a second embodiment, the dual matrix band retainer is capable of restoring two posterior non-adjacent teeth separated by another posterior tooth in the same quadrant of a patient's mouth. This is accomplished by varying the relative location of the first matrix band retainer head portion 24 with respect to the second matrix band retainer head portion 54 by changing the length of bar 21 and 51 on each matrix band retainer 20 and 50, respectively. As shown in FIG. 3, for example, the length of bar 21 allows matrix band 30 to encircle the lower right second molar and the length of bar 51 allows matrix band 60 to encircle the lower right second bicuspid. As a result, the dual matrix band retainer shown in FIG. 3, is in position for restoring, for example, a mesio-occlusal preparation in the second molar and a disto-occlusal cavity preparation in the second bicuspid.

It should be noted that the dual matrix band retainer as described above is capable of restoring posterior teeth in the lower right and, by inverting, the upper left quadrant of a patient's mouth. Furthermore, it can be appreciated by those skilled in the art that a dual matrix band retainer which is a mirror image of that described and shown in the figures above will be able to restore posterior teeth in the lower left and upper right quadrant of a patient's mouth.

Having identified the components of the dual matrix band retainer, its operation in the preferred embodiment can be described. Assuming that each matrix band 30 and 60 has been preshaped into substantially a loop and the dentist desires to apply the matrix to the right lower first molar and second molar, each tightening screw 38 and 68 are rotated, separately and independently of each other, so as to move each matrix band clamping block 22 and 52 toward each head portion 24 and 54, respectively. Next, the matrix band ends 32 and 62 are inserted into the slots provided between the fingers 25, 28 and 55, 58 and depressed into the diagonal slots 31 and 61 in each matrix band clamping block 22 and 52, respectively. Each knob 37 and 67 is rotated, separately and independently of each other, for bringing conical tips 36 and 66 of each spindle 34 and 64 into clamping relation with the matrix band ends 32 and 62.

Next, the loops of each matrix band 30 and 60 are arranged around each tooth. Each matrix band is pressed down until it is disposed close to the gingival border. The dentist rotates each tightening screw 38 and 68, separately and independently of each other, to retract each matrix band clamping block 22 and 52 relative to each head portion 24 and 54, respectively, until each matrix band is drawn tightly around the tooth.

It should be noted that the tightening screws 38, 68 and knobs 37, 67 project beyond the patient's mouth so that the dentist may operate any one without inserting his fingers into the mouth of the patient. A clear view of the tooth is assured and the dentist can observe each matrix band 30 and 60 as it is tightened or loosened around each tooth.

To remove each matrix band 30 and 60 from each matrix band retainer 20 and 50, respectively, knobs 37 and 67 are turned, separately and indepentently of each other, while holding each tightening screw 38 and 68 against rotation. This backs the conical ends 36 and 66 of each spindle 34 and 64 from the ends 32 and 62 of each matrix band 30 and 60, respectively. Each head portion 24 and 54 now may be freed from each matrix band 30 and 60. Each matrix band 30 and 60 may now be removed from each tooth. It may be noted that the manipulations of knobs 37, 67 and tightening screws 38, 68 are accomplished outside the oral cavity.

Although the invention has been described in detail with particular reference to a preferred embodiment thereof, it should be understood that the invention is capable of other and different embodiments, and its details are capable of modifications in various obvious respects. As is readily apparent ot those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

I claim:

1. A dual matrix band retainer for allowing a dentist to treat a plurality of posterior teeth in the same quadrant of a patient's mouth simultaneously, said dual matrix band retainer comprising:

a first matrix band retainer for looping a first matrix band around a first posterior tooth, wherein said first matrix band is not integral and is removable from said first matrix band retainer;

a second matrix band retainer for looping a second matrix band around a second posterior tooth, wherein said second matrix band is not integral and is removable from said second matrix band retainer;

a fastening means for connecting said first matrix band retainer with said second matrix band retainer.

2. A method for allowing a dentist to treat a plurality of posterior teeth in the same quadrant of a patient's mouth simultaneously, said method comprising:

providing a first matrix band retainer for looping a first matrix band around a first posterior tooth, wherein said first matrix band is not integral and is removable from said first matrix band retainer;

providing a second matrix band retainer for looping a second matrix band around a second posterior tooth, wherein said second matrix band is not integral and is removable from said second matrix band retainer;

providing a fastening means for connecting said first matrix band retainer with said second matrix band retainer.

* * * * *